United States Patent [19]

Shaw

[11] Patent Number: 4,739,064

[45] Date of Patent: Apr. 19, 1988

[54] SELECTIVE HYDROGENATION OF HETEROCYCLIC AROMATIC COMPOUNDS

[75] Inventor: James E. Shaw, Bartlesville, Okla.

[73] Assignee: Phillips Petroleum Company, Bartlesville, Okla.

[21] Appl. No.: 804,579

[22] Filed: Dec. 4, 1985

[51] Int. Cl.$^4$ .................. C07D 215/04; C07D 219/02; C07D 217/02; C07D 209/08

[52] U.S. Cl. ..................... 546/102; 546/61; 546/101; 546/108; 546/150; 546/166; 546/58; 546/38; 546/33; 546/439; 546/490; 546/420; 546/418; 208/143; 208/254 M

[58] Field of Search ................. 546/101, 102, 150, 61, 546/166; 548/439, 490; 208/143, 254 H

[56] References Cited

U.S. PATENT DOCUMENTS

| | | | |
|---|---|---|---|
| 2,790,751 | 4/1957 | Gerald | 208/254 H |
| 3,003,953 | 10/1961 | Evans | 208/254 H |
| 3,322,770 | 5/1967 | D'Alessandro et al. | 546/185 |
| 3,383,306 | 5/1968 | Rogers et al. | 208/254 H |
| 3,394,077 | 7/1968 | Kovach et al. | 208/254 H X |
| 3,412,174 | 11/1968 | Kroll | 585/277 |
| 3,437,588 | 4/1969 | Kovach et al. | 208/254 H X |
| 3,444,198 | 5/1969 | Korst | 260/351.5 |
| 3,477,963 | 11/1969 | van Venrooy | 208/143 X |
| 3,481,867 | 12/1969 | Dellert | 208/254 H |
| 3,516,926 | 6/1970 | Davis, Jr. et al. | 208/143 |
| 3,528,910 | 9/1970 | Haney et al. | 208/254 H |
| 3,544,485 | 12/1970 | Taira et al. | 252/477 |
| 3,793,383 | 2/1974 | Johnson et al. | 585/477 |
| 3,929,784 | 12/1975 | Richards | 546/176 |
| 4,181,602 | 1/1980 | Quick et al. | 208/254 H X |
| 4,372,842 | 2/1983 | Gardner | 208/254 H |
| 4,386,207 | 5/1983 | de Graaf | 546/154 |

OTHER PUBLICATIONS

Ponomarev, et al., Khimiya Geterotsiklicheskikh Soedinenti, vol. 2, No. 2, pp. 239-242 (1966).
Cocchetto, et al., Ind. Eng. Chem., Process Des. Dev., vol. 15, No. 2, pp. 272-277 (1976).
Nagai, et al., Chemical Abstracts, vol. 92, 110338y (1980).
Fish, et al.(V), J. Am. Chem. Soc., vol. 104, pp. 5234-5237 (1982).
Fish (Y), Chemical Abstracts, vol. 101, 90107w (1984).
Fish, et al., (Z), Chemical Abstracts, vol. 102, 206351y (1985).
Kirk-Othmer, Encyclopedia of Chemical Technology, 3rd ed., vol. 19, p. 538.
Heterocyclic Compounds, vol. IV, Elderfield (ed.), pp. 282-286.
Catal. Rev.-Sci. Eng., 20(2), 155-208 (1979), "Process and Catalyst Needs for Hydrodenitrogenation", J. R. Katzer and R. Sivasubramanian.

*Primary Examiner*—Mark L. Berch
*Assistant Examiner*—Diana G. Rivers
*Attorney, Agent, or Firm*—Hal Brent Woodrow

[57] ABSTRACT

Selective hydrogenation of the unsaturated nitrogen-containing ring in heterocyclic aromatic compounds is promoted by the use of at least one hydrogenation catalyst selected from the group consisting of nickel, cobalt, palladium, platinum, ruthenium and rhodium in the presence of reaction modifiers exemplified by carbon monoxide, carbon disulfide and hydrogen sulfide.

17 Claims, No Drawings

SELECTIVE HYDROGENATION OF HETEROCYCLIC AROMATIC COMPOUNDS

This invention relates to the selective hydrogenation of unsaturated nitrogen-containing rings in heterocyclic aromatic compounds.

BACKGROUND OF THE INVENTION

Hydrogenation processes for the complete saturation of polynuclear aromatic compounds are well known in the art. For example, naphthalene can be hydrogenated to decalin and quinoline or isoquinoline can be hydrogenated to decahydroquinolines. However, as is well recognized in the art, the selective hydrogenation of only the more readily reducible sites in a feedstock characterized by the presence of different types of unsaturation is not readily accomplished. In general, a complex mixture of products exhibiting varying degrees of saturation is obtained. Catalytic hydrogenation systems possessing the capacity for effecting the selective hydrogenation of nitrogen heterocyclic rings in heterocyclic aromatic compositions are significant contributions to the art because practical routes to useful products can be developed and other processes such as hydrodenitrogenation (HDN) can be rendered more economical.

In a HDN process, the nitrogen in organic nitrogen compounds is converted to ammonia. This nitrogen must be removed by the process of hydrodenitrogenation (HDN) to prevent poisoning of refining catalysts and to avoid the sale of products which form gums and sediments or cause air pollution on burning. Heavy oil, shale oil and coal-derived liquids contain high levels of such nitrogenous compositions. If the feedstream to a HDN process contains homocyclic aromatics as well as heterocyclic aromatic compounds characterized by the presence of unsaturated nitrogencontaining rings, significant amounts of hydrogen can be consumed by the undesirable hydrogenation of the homocyclic aromatics. This undesired nonselective hydrogenation reaction increases the overall cost of the process because hydrogen is expensive. Current HDN methods consume more hydrogen than necessary to remove nitrogen as ammonia because in a typical hydrodenitrogenation process homocyclic aromatic rings are hydrogenated. Thus, HDN processes based on more selective hydrogenation catalysts need to be developed and would be highly preferred.

One value of the instant selective hydrogenation process resides in its potential use as the initial step of a hydrodenitrogenation operation. The application of the instant process as the front end of a HDN operation would result in hydrogenation of the unsaturated nitrogen-containing rings in the heterocyclic aromatic compositions without promoting hydrogenation of the homocyclic aromatics. This would result in lower process costs because less hydrogen would be consumed. The second step of the HDN process involving hydrogenolysis of C-N bonds to complete the removal of nitrogen as ammonia would be effected by other chemical means.

INVENTION

In accordance with the present invention, I have discovered that heterocyclic aromatic compounds characterized by the presence of unsaturated nitrogen-containing rings are selectively hydrogenated in the heterocyclic ring by contacting such feedstocks with at least one hydrogenation catalyst selected from the group consisting of platinum, palladium, rhodium, ruthenium, cobalt and nickel under hydrogenation conditions in the presence of at least one reaction modifier selected from the group consisting of elemental sulfur, carbon monoxide, carbon disulfide, hydrogen sulfide, thiophene, tetrahydrothiophene, monomercaptans, polymercaptans, dialkyl sulfides and dialkyl disulfides.

The heterocyclic aromatic compounds which can be selectively hydrogenated in the unsaturated nitrogen-containing ring are those of the formulas I, II, III and IV

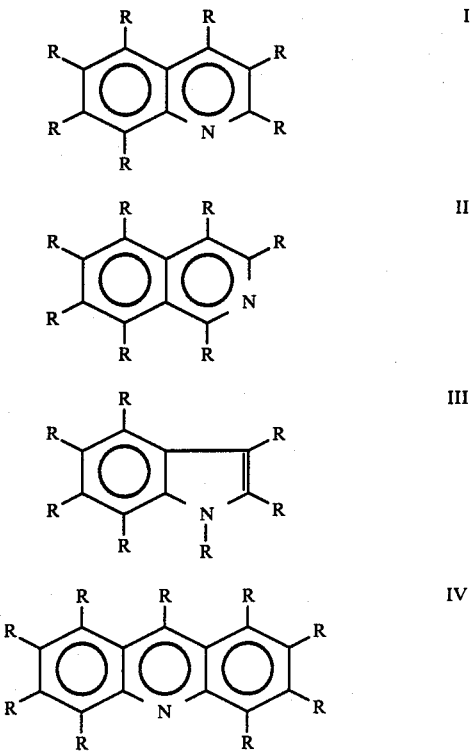

wherein R represents hydrogen, alkyl groups containing 1 to 20 carbon atoms and R groups on adjacent carbon atoms can be divalent 1,4-(alkadienyl-1,3) radicals with the proviso that the total number of carbon atoms in the compound does not exceed 40.

Representative heterocyclic aromatic compounds include quinoline, isoquinoline, indole, 2-methylquinoline, acridine, carbazole, phenanthridine, 4-methylquinoline, 2,4-dimethylquinoline and 2-isobutylquinoline.

Other materials suitable for use in the present invention include heavy oil, shale oil and coal-derived liquids which contain the disclosed heterocyclic aromatic compounds or derivatives thereof.

In addition to hydrogen sulfide and carbon disulfide, other suitable divalent sulfur-containing reaction modifiers include, e.g., monomercaptans such as methyl mercaptan and ethyl mercaptan, cyclic thioethers such as thiophene and tetrahydrothiophene, polymercaptans such as 1,2-ethanedithiol and 1,2-dimercaptocyclohexane, dialkyl sulfides such as dimethyl sulfide, as well as dialkyl disulfides such as dimethyl disulfide and diethyl disulfide. These reaction modifiers can contain up to 30 carbon atoms. Hydrogen sulfide and carbon disulfide are the preferred sulfur-containing reaction modifiers.

The reaction modifier and heterocyclic aromatic compound are usually contacted with the catalyst at the same time, but alternatively, the catalyst can be treated with the reaction modifier before addition of the heterocyclic aromatic compound.

If desired, the invention can be carried out in the presence of a solvent. Representative solvents suitable for use in the instant selective hydrogenation process include paraffins containing preferably five to sixteen carbon atoms such as cyclohexane, pentane, hexane, octane, decane, dodecane and hexadecane. Suitable aromatic solvents include benzene, toluene and xylenes. It is contemplated that the instant process can also be practiced in the absence of an added solvent.

In practicing the instant invention, the temperature varies over the broad range of 25° C. to 300° C., preferably over the range of 100° C. to 250° C. The initial hydrogen pressure of the reaction system is adjusted into the broad range of atmospheric to 3000 psi (gauge), preferably over the range of 200 to 2000 psi (gauge) at room temperature. The time of reaction varies over the broad range of 0.1 hour to 10 hours with a preferred range of 1 to 3 hours. It is recognized, of course, that the necessary reaction time will vary with the temperature, hydrogen pressure and catalyst concentration.

Suitable amounts of the sulfur-containing compounds and carbon monoxide reaction modifiers can be expressed, respectively, as a ratio of g-atoms of sulfur to metal hydrogenation catalyst and moles CO to g-atoms of metal hydrogenation catalyst. In regard to the elemental sulfur or sulfur-containing reaction modifier embodiment, the sulfur to metal gram atom ratio varies over the broad range of 0.1:1 to $10^4$:1 preferably over the range of 1:1 to 100:1. There is no upper limit to the sulfur/metal gram-atom ratio other than that dictated by reason, convenience and economical considerations. In regard to the carbon monoxide reaction modifier embodiment, the mole to gram-atom ratio of carbon monoxide to metal varies over the broad range of 90:1 to $10^4$:1 preferably over the range of 100:1 to 1000:1.

The following Examples I-III disclose representative inventive runs wherein the selective hydrogenation of the unsaturated nitrogen-containing heterocyclic ring in quinolines was effected with metal hydrogenation catalysts in the presence of reaction modifiers such as $H_2S$, $CS_2$ and CO. The results of these invention runs are summarized in Table I.

EXAMPLE I

Hydrogenation of 2-Methylquinoline with $Pt/Al_2O_3$ and $CS_2$

To a 300 mL autoclave was added 10.0 g (0.070 mol) 2-methylquinoline, 90.0 g n-hexadecane, 0.20 g Pt/Al$_2$O$_3$ (5 weight percent Pt) and 20 microliters (0.025 g) carbon disulfide. After mixing, the autoclave was pressured with hydrogen to 700 psi, stirred a few seconds and the pressure was released. This was repeated three more times. The autoclave was pressured with hydrogen to 750 psi at room temperature and then heated with rapid stirring to 160° C. cover a period of 0.5 hour and maintained at 160° C. for 1.2 hours. After cooling to room temperature, the contents of the reactor were suction filtered. The autoclave and catalyst were washed with acetone and the washings stripped to a residual oil which was combined with the primary filtrate. Gas liquid chromatographic analysis showed that the product consisted of 97 percent 2-methyl1,2,3,4-tetrahydroquinoline and 3 percent 2-methylquinoline (starting material). Gas liquid chromatographic analysis using an external standard showed that the absolute yield of 2-methyl-1,2,3,4-tetrahydroquinoline was 100 percent based on converted starting material (Table I, run 6).

EXAMPLE II

Hydrogenation of 2-Methylquinoline with $Pd/Al_2O_3$ and CO

To a 300 mL autoclave was added 10.0 g (0.07 mol) 2-methylquinoline, 90.0 g n-hexadecane and 0.20 g Pd/Al$_2$O$_3$ (5 weight percent palladium). The autoclave was flushed four times with hydrogen as described above. Carbon monoxide was then flushed through the autoclave to displace hydrogen and the CO pressure was brought to 50 psi before adding sufficient hydrogen to reach 800 psi $H_2$.

The autoclave was heated with rapid stirring to 200° C. over a period of 0.5 hour and then maintained at 200° C. for 3.2 hours. After working up the reaction mixture as described in (A), the product was analyzed by gas liquid chromatography and found to contain 94 percent 2-methyl-1,2,3,4-tetrahydroquinoline and 6 percent 2-methylquinoline (starting material) (Table I, run 3).

A second run with the CO at 7 psi gauge pressure gave essentially the same result.

A third run with the CO pressure at zero pressure but at atmospheric pressure gave a mixture of 99.4 percent 2-methyl-1,2,3,4-tetrahydroquinoline and 0.6 percent 2-methyl-5,6,7,8-tetrahydroquinoline. In this run the reaction temperature was 176° C. for 3 hours.

EXAMPLE III

Hydrogenation of 4-Methylquinoline with $Pt/Al_2O_3$ and $H_2S$

To a 300 mL autoclave was added 7.5 g 4-methylquinoline, 67.5 g n-hexadecane and 0.15 g Pt/Al$_2$O$_3$. The autoclave was pressured with hydrogen to 700 psi and then the pressure was released. This was repeated four more times. After the hydrogen pressure was released, $H_2S$ gas was passed into the autoclave so that 0.1 g was added. The autoclave was pressured to 769 psi with hydrogen, heated with stirring over a period of 0.5 hour to 160° C. and then maintained at 160° C. for 2.5 hours.

After cooling to room temperature, the contents of the autoclave were suction filtered. The autoclave and catalyst were washed with acetone and the washing stripped to a residual oil which was combined with the primary filtrate. Gas liquid chromatographic analysis of this odorless liquid on a 6'×⅛"10% Carbowax 20M column at 200° C. showed that the only reaction product was 4-methyl-1,2,3,4-tetrahydroquinoline. The mixture contained 8% 4-methylquinoline (starting material) but no 4-methyl-5,6,7,8-tetrahydroquinoline was detectable by the gas liquid chromatographic analysis (Table I, run 15).

TABLE I

Selective Hydrogenation* of Nitrogen—Heterocyclic Rings in Quinolines

| Quinoline[a] | Run No. | Catalyst[b] | Type of Run | Reaction Modifier | Temp. °C. | Reaction Time Hr.[c] | Product Ratio[d] % 1,2,3,4-Tetrahydro | % 5,6,7,8-Tetrahydro |
|---|---|---|---|---|---|---|---|---|
| 2-MQ | 1 | Pd/Al$_2$O$_3$ | Control | None | 160 | 1.0 | 54 | 46 |
| 2-MQ | 2 | Pd/Al$_2$O$_3$ | Invention | CS$_2$ | 160 | 3.3 | 100[e] | 0 |
| 2-MQ | 3 | Pd/Al$_2$O$_3$ | Invention | CO# | 200 | 3.2 | 100 | 0 |
| 2-MQ | 4 | Pt/Al$_2$O$_3$ | Control | None | 150 | 1.0 | 92[e] | 8 |
| 2-MQ | 5 | Pt/Al$_2$O$_3$ | Invention | H$_2$S | 160 | 1.5 | 100 | 0 |
| 2-MQ | 6 | Pt/Al$_2$O$_3$ | Invention | CS$_2$ | 160 | 1.2 | 100[e] | 0 |
| 2-MQ | 7 | Pt/Al$_2$O$_3$ | Invention | CS$_2$[f] | 200 | 2.2 | 100 | 0 |
| 2-MQ | 8 | Ru/Al$_2$O$_3$ | Control | None | 160 | 1.6 | 74[g] | 26 |
| 2-MQ | 9 | Ru/Al$_2$O$_3$ | Invention | CS$_2$ | 160 | 3.2 | 100[h] | 0 |
| 2-MQ | 10 | Rh/Al$_2$O$_3$ | Control | None | 100 | 0.5 | 63 | 37 |
| 2-MQ | 11 | Rh/Al$_2$O$_3$ | Invention | CS$_2$ | 150 | 4.2 | 100[e] | 0 |
| 2-MQ | 12 | Ni/SiO$_2$—Al$_2$O$_3$ | Control | None | 160 | 1.5 | 74 | 26 |
| 2-MQ | 13 | Ni/SiO$_2$—Al$_2$O$_3$ | Invention | CS$_2$ | 175 | 2.5 | 100[e] | 0 |
| 4-MQ | 14 | Pt/Al$_2$O$_3$ | Control | None | 160 | 2.0 | 97 | 3 |
| 4-MQ | 15 | Pt/Al$_2$O$_3$ | Invention | H$_2$S | 160 | 2.5 | 100 | 0 |
| 2,4-DMQ | 16 | Pt/Al$_2$O$_3$ | Control | None | 160 | 1.5 | 88 | 12 |
| 2,4-DMQ | 17 | Pt/Al$_2$O$_3$ | Invention | CS$_2$ | 160 | 1.7 | 100 | 0 |

*Initial hydrogen pressure at room temperature was 750 psi.
[a]2-MQ,4-MQ and 2,4-DMQ represent, respectively, 2-methylquinoline, 4-methylquinoline and 2,4-dimethylquinoline.
[b]All catalysts were 5% by weight metal except for Ni/SiO$_2$—Al$_2$O$_3$ which was 60 to 65 wt. % Ni.
[c]To estimated total reaction time 0.5 hour required to reach the desired temperature should be added to each entry.
[d]Unless otherwise noted, no other products were detectable except for 2–3% starting material.
[e]Absolute yield was 100% based on consumed starting material.
[f]Instead of the usual 0.025 g CS$_2$, 0.2 g CS$_2$ was used in this run. An additional run with 1.0 g CS$_2$ gave the same result at 225° C.
[g]Decahydroquinoline (12% of products) was also detectable.
[h]No decahydroquinoline was present.
Initial hydrogen pressure at room temperature was 800 psi; CO pressure was 50 psi.

Referring to runs 1, 2 and 3 in Table I, it is evident that the Pd/Al$_2$O$_3$ catalyst in the presence of CS$_2$ (run 2) or CO (run 3) was effective for the exclusive hydrogenation of the nitrogen-containing heterocyclic ring in 2-methylquinoline whereas the control Pd/Al$_2$O$_3$ catalyst (run 1) system resulted in reduction of both the aromatic benzenoid ring (leading to the production of the 5,6,7,8-tetrahydro isomer) and the nitrogen-heterocyclic ring (leading to the production of the 1,2,3,4-tetrahydro isomer).

Referring to runs 4, 5, 6 and 7 in Table I, it is evident that the Pt/Al$_2$O$_3$ catalyst in the presence of CS$_2$ (runs 6 and 7) or H$_2$S (run 5) was effective for the exclusive hydrogenation of the nitrogen-containing heterocyclic ring in 2-methylquinoline whereas the control Pt/Al$_2$O$_3$ catalyst (run 4) system resulted in reduction of both the benzenoid aromatic ring and the nitrogen heterocyclic ring.

Referring to runs 8 and 9 in Table I, it is evident that the Ru/Al$_2$O$_3$ catalyst in the presence of CS$_2$ (run 9) effected the exclusive hydrogenation of the nitrogen-containing heterocyclic ring in 2-methyl-quinoline whereas the control Ru/Al$_2$O$_3$ catalyst (run 8) system resulted in reduction of both the benzenoid aromatic ring and the nitrogen heterocyclic ring.

Referring to runs 10, 11, 12, and 13 in Table I, it is evident, respectively, that the Rh/Al$_2$O$_3$ (run 11) and Ni/SiO$_2$-Al$_2$O$_3$ (run 13) catalysts in the presence of carbon disulfide were effective for the exclusive hydrogenation of the nitrogen-containing heterocyclic ring in 2-methylquinoline whereas the control catalysts, respectively, Rh/Al$_2$O$_3$ (run 10) and Ni/SiO$_2$-Al$_2$O$_3$ (run 12) resulted in reduction of both the benzenoid aromatic ring and the nitrogen heterocyclic ring.

Referring to runs 14, 15, 16 and 17 in Table I, it is evident respectively, that the nitrogen-containing heterocyclic rings in the 4-methylquinoline (run 15) and 2,4-dimethylquinoline (run 17) were exclusively hydrogenated in the presence of H$_2$S (run 15) and CS$_2$ (run 17) with a Pt/Al$_2$O$_3$ catalyst whereas the control catalyst Pt/Al$_2$O$_3$ (runs 14 and 16) resulted in the reduction of both the benzenoid aromatic ring and nitrogen-containing heterocyclic ring.

A series of control runs, as exemplified in Example IV, was carried out in a 300 mL stainless steel autoclave to determine the extent to which the benzenoid aromatic ring and the nitrogen-heterocyclic ring in alkyl-substituted quinolines undergo hydrogenation with conventional catalysts. The results are summarized in Table II.

TABLE II

Hydrogenation* of Alkyl-substituted Quinolines Over Conventional Catalysts

| Feedstock[a] | Catalyst[b] | Run No. | Temp °C. | Reaction Time Hr.[c] | % Distribution of Products[d] 1,2,3,4-Tetrahydro | 5,6,7,8-Tetrahydro |
|---|---|---|---|---|---|---|
| 2-MQ | Pd/Al$_2$O$_3$ | 1 | 160 | 1.0 | 54 | 46 |
| 2-MQ | Pt/Al$_2$O$_3$ | 2 | 150 | 1.0 | 92[e] | 8 |
| 2-MQ | Pt/C | 3 | 150 | 1.0 | 96[e] | 4 |
| 2-MQ | Ru/Al$_2$O$_3$ | 4 | 160 | 1.6 | 74 | 26[f] |
| 2-MQ | Rh/Al$_2$O$_3$ | 5 | 100 | 0.5 | 63 | 37 |
| 2-MQ | Ni/SiO$_2$—Al$_2$O$_3$ | 6 | 160 | 1.5 | 74 | 26 |
| 2-MQ | Raney Ni | 7 | 160 | 2.2 | 63 | 37 |
| 2-MQ | NiO—MoO$_3$/Al$_2$O$_3$ | 8 | 300 | 3.0 | 92[h] | 8[i] |
| 2-MQ | NiO—MoO$_3$/Al$_2$O$_3$[g] | 9 | 300 | 1.5 | 98[h] | 2 |
| 4-MQ | Pt/Al$_2$O$_3$ | 10 | 160 | 2.0 | 97 | 3 |
| 4-MQ | Ni/SiO$_2$—Al$_2$O$_3$ | 11 | 160 | 1.5 | 64 | 36 |
| 6-MQ | Pd/Al$_2$O$_3$ | 12 | 105 | 1.0 | 98.5 | 1.5 |

TABLE II-continued

Hydrogenation* of Alkyl-substituted Quinolines Over Conventional Catalysts

| Feedstock[a] | Catalyst[b] | Run No. | Reaction Temp °C. | Time Hr.[c] | % Distribution of Products[d] 1,2,3,4-Tetrahydro | 5,6,7,8-Tetrahydro |
|---|---|---|---|---|---|---|
| 2,4-DMQ | Pt/Al$_2$O$_3$ | 13 | 160 | 1.5 | 88 | 12 |

*Initial hydrogen pressure was 750 psi (gauge) at room temperature.
[a]2-MQ; 4-MQ; 6-MQ and 2,4-DMQ represent, respectively, 2-methylquinoline; 4-methylquinoline; 6-methylquinoline and 2,4-dimethylquinoline.
[b]Catalysts were 5% metal except for Ni/SiO$_2$—Al$_2$O$_3$ which was 60 to 65% Ni and Ni—Mo/Al$_2$O$_3$ which was 2.4% Ni (as NiO) and 11.6% Mo (as MoO$_3$).
[c]To estimate total reaction time 0.5 hour required to reach the desired temperature should be added to each entry.
[d]Unless otherwise noted, no other products were detectable except for 2–3% starting material.
[e]Absolute yield was 100% based on consumed starting material.
[f]Decahydroquinoline was detectable (12%).
[g]In this run only, the catalyst was presulfided using 10% H$_2$S and 90% H$_2$ at 375° C. See Example VII.
[h]In these runs, 6–7% starting material was unreacted.
[i]At 250° C. the ratio of the 1,2,3,4-tetrahydro derivative to the 5,6,7,8-tetrahydro derivative was 99:1.

Referring to the runs in Table II, it is evident that none of the control hydrogenation systems yielded 100% of the 1,2,3,4-tetrahydro derivatives to the exclusion of the 5,6,7,8-tetrahydro derivatives. Even in run 9, (see Example VII hereinbelow), wherein a NiO-MoO$_3$-/Al$_2$O$_3$ catalyst was presulfided, 2 percent of the 5,6,7,8-tetrahydro compound was detectable by gas liquid chromatography. In run 8 at 250° C. rather than 300° C., it is noteworthy that the ratio of the 1,2,3,4-tetrahydro derivative to the 5,6,7,8-tetrahydro derivative reached a maximum of 99:1 but reverted to 92:8 at the reaction temperature of 300° C.

EXAMPLE IV

Hydrogenation of 2-Methylquinoline with Pt/Al$_2$O$_3$ (Control)

To a 300 mL autoclave was added 10.0 g (0.070 mol) of 2-methyl-quinoline, 90.0 g n-hexadecane and 0.2 g 5 percent platinum on alumina. The autoclave was pressured with hydrogen to 700 psi, the contents were stirred briefly and then the pressure was released. This was repeated three more times. The autoclave was then pressured with hydrogen to 750 psi at ambient temperature and then heated with rapid stirring (1100 rpm) to 150° C. over a period of 0.5 hour and thereafter maintained at 150° C. for one hour.

The autoclave was cooled to room temperature and the contents were suction filtered. To obtain complete recovery, the autoclave nd catalyst were flushed with acetone and this solution was stripped to a residual liquid which was combined with the primary filtrate. Gas liquid chromatography/mass spectral (GLC/MS) analysis showed that the reaction mass (exclusive of n-hexadecane) consisted of 90 percent 2-methyl-1,2,3,4-tetrahydroquinoline, 8 percent 2-methyl-5,6,7,8-tetrahydroquinoline and 2 percent 2-methylquinoline (starting material). The ratio of the 1,2,3,4-tetrahydro derivative to the 5,6,7,8-tetrahydro derivative was 92:8 (see run 2 in Table II). The 2-methyl-1,2,3,4-tetrahydroquinoline was identified by comparison with an authenic sample (infrared, nuclear magnetic resonance and mass spectral analyses). The 2-methyl-5,6,7,8-tetrahydroquinoline material was verified by similar analyses giving:

IR(neat) 1594, 1573, 803 cm$^{-1}$; NMR (CDCl$_3$) δ 1.58–2.18 (m, 4H), 2.51 (s,3H), 2.53–3.20 (m,4H); 6.87, 7.27 (ABq, 2H, J=8 Hz); MS, m/e 147 (M+). Anal. Calcd. for C$_{10}$H$_{13}$N: C, 81,58; H,8.90; N, 9.52. Found: C, 81.32; H,8.98; N, 9.43.

EXAMPLE V

This example is concerned with runs wherein the selective hydrogenation of the nitrogen-heterocyclic ring in indole was effected with Pd/Al$_2$O$_3$, Ni/SiO$_2$Al$_2$O$_3$ and Pt/Al$_2$O$_3$ catalysts in the presence of carbon disulfide as the reaction modifier. The results of these runs are summarized in Table III along with selected control runs.

The following procedure is typical of the manner in which the runs of Table III were carried out.

To a 300 mL autoclave was added 10.0 g (0.085 mol) indole, 90.0 g n-hexadecane and 0.6 g Pt/Al$_2$O$_3$ (5 weight percent platinum). The autoclave was pressured with hydrogen to 700 psi, stirred briefly and then the pressure was released. This was repeated three more times. The autoclave was pressured with hydrogen to 1890 psi at room temperature, heated with rapid stirring to 227° C. over a period of 0.5 hour and then maintained at 227° C. for 10.5 hours. The final pressure at 227° C. was 2200 psi.

The autoclave was cooled to room temperature and the reactor contents were suction filtered. The autoclave and catalyst were flushed with acetone and this solution was stripped to a residual liquid which was added to the primary filtrate. Gas liquid chromatographic analysis and gas liquid chromatography/mass spectral (GLC/MS) analysis showed the presence of 82 percent indoline and 18 percent indole in the product mixture. An identical reaction carried out for 4.5 hours at 227° C. gave the same percentages of indoline and indole. Gas liquid chromatographic analysis using external standards showed that these two compounds accounted for 99 percent of the starting material.

The indoline was isolated by extraction of the n-hexadecane solution with 5 percent aqueous hydrochloric acid. The HCl extract was washed four times with methylene chloride, neutralized with 25 percent aqueous sodium hydroxide to pH of 8–9 and then extracted with methylene chloride. The methylene chloride extract was washed with water, dried over anhydrous sodium sulfate and evaporated in vacuo on a rotary evaporator to give the indoline component which was identical to an authentic sample (IR, NMR, MS analyses).

Referring to the invention runs 5, 6 and 7 in Table III, it is evident that the nitrogen-heterocyclic ring in indole was hydrogenated with a high degree of selectivity. The Ni/SiO$_2$-Al$_2$O$_3$ in the presence of CS$_2$ (run 6) was the most selective as indole and indoline were the only detectable components at the end of the reaction. In runs 5 and 7, the "other" component in the product mixtures was 2-ethylaniline formed presumably by the hydrogenolysis of the desired indoline.

Referring to the control runs 1, 2, 3, 4 and 8 in Table III, it is evident that the Pt/Al$_2$O$_3$ system (runs 1 and 2) was the most selective for reducing the nitrogen-heterocyclic ring in indole as the product mixtures contained only indole and indoline. In control runs 3 and 4, respectively, over Ni/SiO$_2$Al$_2$O$_3$ and Pd/Al$_2$O$_3$ catalysts, low but detectable amounts of tetrahydroindole (resulting from benzenoid aromatic ring hydrogenation) were present in the product mixtures. In run 8, a presulfided NiO-MoO$_3$/Al$_2$O$_3$ catalyst (control) gave comparable results to the instant catalyst system shown in run 7 of Table III.

The production of tetrahydroindole (noted in control runs 3 and 4) resulted from the undesirable hydrogenation of the benzenoid aromatic ring. No tetrahydroindole was detectable in the products of the invention runs 5, 6 and 7 indicating that no reduction of the benzenoid aromatic ring took place.

the benzenoid aromatic rings did not occur under the reaction conditions.

EXAMPLE VII

This example describes the nonselective hydrogenation of 2-methylquinoline over a presulfided NiO-MoO$_3$/Al$_2$O$_3$ catalyst (Table II, run 9).

(A) Presulfiding the NiO-MoO$_3$/Al$_2$O$_3$ Catalyst

To a 300 mL autoclave was added 90.0 g n-hexadecane and 1.00 g powdered NiO-MoO$_3$/Al$_2$O$_3$ catalyst. The autoclave was pressured to 700 psi with hydrogen and then the pressure was released. This was repeated three more times. The autoclave was pressured with hydrogen sulfide to 200 psi and the hydrogen was added to make the total pressure 900 psi. The autoclave was heated to 375° C. over a period of one hour and then maintained at 375° C. for one hour. After cooling the system to room temperature, the hydrogen and hydrogen sulfide pressure were released. The autoclave was

TABLE III

Selective Hydrogenation of the Nitrogen—Heterocyclic Ring in Indole

| Run No. | Catalyst$^a$ (wt. g.) | Type of Run | Reaction Modifier | Temp. °C. | Time$^b$ Hr. | Pressure$^c$ psi | % Products Indoline | Indole | Other |
|---|---|---|---|---|---|---|---|---|---|
| 1 | Pt/Al$_2$O$_3$ (0.6) | Control | None | 227 | 10.5$^d$ | 2200 | 82$^e$ | 18 | ND* |
| 2 | Pt/Al$_2$O$_3$ (0.6) | Control | None | 227 | 5.0 | 1200 | 65 | 35 | ND* |
| 3 | Ni/SiO$_2$—Al$_2$O$_3$ (1.0) | Control | None | 160 | 0.7 | 1395 | 92$^e$ | 7 | 1$^f$ |
| 4 | Pd/Al$_2$O$_3$ (0.5) | Control | None | 143 | 6.0 | 1725 | 76 | 21 | 3$^f$ |
| 5 | Pd/Al$_2$O$_3$ (0.5) | Invention | CS$_2$$^g$ | 300 | 6.0 | 2600 | 55 | 44 | 1$^h$ |
| 6 | Ni/SiO$_2$—Al$_2$O$_3$ (1.0) | Invention | CS$_2$$^g$ | 182 | 4.7 | 1575 | 88 | 12 | ND* |
| 7 | Pt/Al$_2$O$_3$ (0.8) | Invention | CS$_2$$^g$ | 300 | 5.5 | 2715 | 57 | 39 | 4$^h$ |
| 8 | Ni—Mo/Al$_2$O$_3$ (1.0) | Control | i | 232 | 6.0 | 2160 | 56 | 37 | 7$^h$ |

*ND indicates that no additional products were detectable by gas liquid chromatographic analysis.
$^a$All catalysts were 5 weight percent metal except for Ni/SiO$_2$—Al$_2$O$_3$ which was 60–65 weight percent Ni and Ni—Mo/Al$_2$O$_3$ which is 2.4 weight percent Ni (as NiO) and 11.6 weight percent Mo (as MoO$_3$).
$^b$An additional 0.5 hour was required to reach the desired temperature.
$^c$These values correspond to the pressure at the end of the runs at the indicated temperatures.
$^d$The product mixtures were the same after 4.5 hours and after 10.5 hours.
$^e$The use of external standards showed that 99–100% of the starting material was accounted for by the products.
$^f$A tetrahydroindole based on mass spectral analysis (benzenoid aromatic ring was hydrogenated).
$^g$In runs 5, 6 and 7, respectively, 12, 45 and 50 mg aliquots of CS$_2$ were used.
$^h$2-Ethylaniline
$^i$The NiO—MoO$_3$/Al$_2$O$_3$ catalyst was presulfided using 10% H$_2$S/90% H$_2$ at 350° C.

EXAMPLE VI

This example describes the selective hydrogenation of the nitrogen-containing heterocyclic ring in acridine over Pt/Al$_2$O$_3$ in the presence of carbon disulfide.

To a 300 mL autoclave was added 5.0 g (0.028 mol) acridine, 90.0 g n-hexadecane, 0.5 g Pt/Al$_2$O$_3$ (5 weight percent platinum) and 30 microliters (0.038 g) carbon disulfide. After mixing, the autoclave was pressured with hydrogen to 700 psi, stirred a few seconds and the pressure was released. This was repeated three more times. The autoclave was pressured to 800 psi with hydrogen at room temperature, heated with rapid stirring to 170° C. (1090 psi) over a period of 0.5 hour and then maintained at 170° C. for 7.3 hours.

The autoclave was cooled to room temperature and the reaction mixture was diluted with 50 g toluene before a suction filtration was carried out. A gray solid was recovered. This gray solid was further processed by dissolving in ether and filtering the ethereal extract. Evaporation of the ether extract provided 4.4 g (87 percent yield) of 9,10-dihydroacridine as white crystals, m.p. 170°–171° C. (lit. m.p. 169°–171° C.). Gas liquid chromatographic analysis of the ethereal filtrate using a 1'×⅛" 10% Carbowax 20M column showed only 9,10-dihydroacridine was 97 percent. The hydrogenation of pressured with hydrogen and then the pressure was released. This was repeated one more time.

(B) Hydrogenation of 2-Methylquinoline over Presulfided

NiO-MoO$_3$/Al$_2$O$_3$ Catalyst

Ten grams (10.0 g) of 2-methylquinoline was added to the above presulfided catalyst system by syringe through an autoclave port. The autoclave was pressured with hydrogen and then the pressure was released. This was repeated three more times. The autoclave was pressured with hydrogen to 770 psi, heated to 300° C. over a period of 0.5 hour and then maintained at 300° C. for 1.5 hours.

After cooling to room temperature, the reaction mixture was suction filtered to give a slightly yellow but clear filtrate with a strong odor of hydrogen sulfide. Gas liquid chromatographic analysis on a 6'×⅛" 10% Carbowax 20M column showed that it contained 89.5% 2-methyl-1,2,3,4-tetrahydroquinoline, 1.8% 2-methyl-5,6,7,8-tetrahydroquinoline, 6.0% 2-methylquinoline (starting material) and 2.7% 2-methyldecahydroquinoline. The ratio of 2-methyl-1,2,3,4-tetrahydroquinoline to 2-methyl-5,6,7,8-tetrahydroquinoline was 98:2.

This example demonstrates that the presulfiding of a commercially available catalyst such as NiO-MoO$_3$/Al$_2$O$_3$ with H$_2$S failed to give a system suitable for promoting the exclusive hydrogenation of the nitrogencontaining heterocyclic ring in 2-methylquinoline.

Reasonable variations and modifications are possible within the scope of the disclosure and the appended claims to the invention.

That which is claimed is:

1. A process for the selective hydrogenation of the nitrogen-containing ring in at least one heterocyclic aromatic compound of the formulas I, II, III and IV

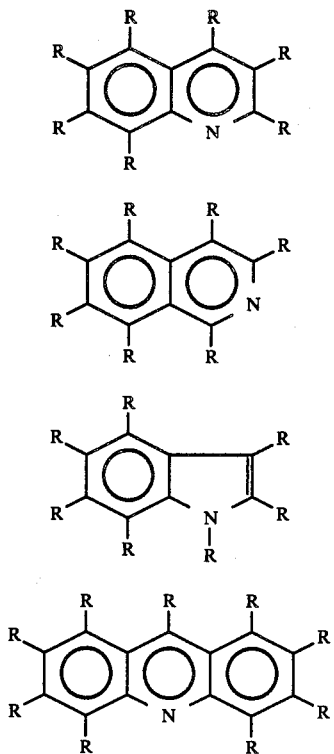

wherein R represents hydrogen, alkyl groups containing 1 to 20 carbon atoms and adjacent R groups can be divalent 1,4-(alkadienyl-1,3) radicals with the proviso that the total number of carbon atoms in said compound does not exceed 40, which comprises contacting said heterocyclic aromatic compound with hydrogen under hydrogenation conditions with a hydrogenation catalyst selected from the group consisting of nickel, cobalt, palladium, platinum, and rhodium in the presence of a reaction modifier selected from the group consisting of carbon disulfide, hydrogen sulfide, thiophene, tetrahydrothiophene, dialkyl disulfides, elemental sulfur, monomercaptans, dialkyl sulfides and polymercaptans containing up to 30 carbon atoms, at a temperature of from 25° C. to 300° C.

2. A process in accordance with claim 1 wherein the gram atom ratio of sulfur in the reaction modifier to metal in the metal hydrogenation catalyst varies over the range of 0.1:1 to $10^4$:1.

3. A process in accordance with claim 1 wherein the hydrogen pressure varies over the range of atmospheric to 3000 psi.

4. A process in accordance with claim 1 wherein said heterocyclic aromatic compounds include quinoline, isoquinoline, indole, 2-methylquinoline, acridine, carbazole, 4-methylquinoline, phenanthridine, 2,4-dimethylquinoline and 2-isobutylquinoline.

5. A process in accordance with claim 1 wherein said heterocyclic aromatic compound is 2-methylquinoline, said hydrogenation catalyst is palladium on alumina and said reaction modifier is carbon disulfide.

6. A process in accordance with claim 1 wherein said heterocyclid aromatic compound is 2-methylquinoline, said hydrogenation catalyst is platinum on alumina and said reaction modifier is hydrogen sulfide.

7. A process in accordance with claim 1 wherein said heterocyclic aromatic compound is 2-methylquinoline, said hydrogenation catalyst is platinum on alumina and said reaction modifier is carbon disulfide.

8. A process in accordance with claim 1 wherein said heterocyclic aromatic compound is 2-methylquinoline, said hydrogenation catalyst is rhodium on alumina and said reaction modifier is carbon disulfide.

9. A process in accordance with claim 1 wherein said heterocyclic aromatic compound is 2-methylquinoline, said hydrogenation catalyst is nickel on silica-alumina and said reaction modifier is carbon disulfide.

10. A process in accordance with claim 1 wherein said heterocyclic aromatic compound is 4-methylquinoline, said hydrogenation catalyst is platinum on alumina and said reaction modifier is hydrogen sulfide.

11. A process in accordance with claim 1 wherein said heterocyclic aromatic compound is 2,4-dimethylquinoline, said hydrogenation catalyst is platinum on alumina and said reaction modifier is carbon disulfide.

12. A process in accordance with claim 1 wherein said heterocyclic aromatic compound is indole, said hydrogenation catalyst is palladium on alumina and said reaction modifier is carbon disulfide.

13. A process in accordance with claim 1 wherein said heterocyclic aromatic compound is indole, said hydrogenation catalyst is nickel on silica-alumina and said reaction modifier is carbon disulfide.

14. A process in accordance with claim 1 wherein said heterocyclic aromatic compound is indole, said hydrogenation catalyst is platinum on alumina and said reaction modifier is carbon disulfide.

15. A process in accordance with claim 1 wherein said heterocyclic aromatic compound is acridine, said hydrogenation catalyst is platinum on alumina and said reaction modifier is carbon disulfide.

16. A process in accordance with claim 1 wherein said selective hydrogenation is carried out in a solvent selected from the group consisting of pentane, cyclohexane, hexane, heptane, octane, decane, dodecane, hexadecane, benzene, toluene and xylenes.

17. A process in accordance with claim 1 wherein said heterocyclic aromatic compounds are components present in heavy oil, shale oil and coal-derived liquids.

* * * * *